United States Patent [19]
Bossen et al.

[11] Patent Number: 5,165,277
[45] Date of Patent: Nov. 24, 1992

[54] SYSTEM AND PROCESS FOR DETERMINING PROPERTIES OF A MOVING SHEET OF MATERIAL

[75] Inventors: David A. Bossen, Palo Alto; Mathew G. Boissevain, Los Altos; Paul J. Houghton, Los Gatos; Henry R. Markus, Cupertino, all of Calif.

[73] Assignee: Measurex Corporation, Cupertino, Calif.

[21] Appl. No.: 736,045

[22] Filed: Jul. 25, 1991

Related U.S. Application Data

[63] Continuation-in-part of Ser. No. 645,949, Jan. 25, 1991, which is a continuation-in-part of Ser. No. 575,101, Aug. 29, 1990, abandoned.

[51] Int. Cl.$^5$ ............... G01N 33/34; G01N 33/44
[52] U.S. Cl. ......................... 73/159; 248/647
[58] Field of Search .................... 73/159; 248/647

[56] References Cited

U.S. PATENT DOCUMENTS

| | | |
|---|---|---|
| 260,080 | 6/1882 | Barrie et al. |
| 816,485 | 3/1906 | Lindall et al. |
| 3,468,756 | 9/1969 | Villa ............... 162/344 |
| 3,621,259 | 11/1971 | Boissevain |
| 3,698,326 | 10/1972 | Schurch et al. |
| 3,828,248 | 8/1974 | Wennerberg ............... 73/159 |
| 3,854,406 | 12/1974 | Monne |
| 4,008,123 | 2/1977 | Kirjavainen ............... 162/336 |
| 4,062,235 | 12/1977 | Hazelett et al. ............... 73/159 |
| 4,248,157 | 2/1981 | Evans |
| 4,253,913 | 3/1981 | Chaudhuri ............... 73/159 |
| 4,271,699 | 6/1981 | Williamson ............... 73/159 |
| 4,400,890 | 8/1983 | Ohkubo et al. ............... 33/708 |
| 4,449,398 | 5/1984 | Williams ............... 73/159 |
| 4,455,197 | 6/1984 | Croteau et al. ............... 162/344 |
| 4,484,525 | 11/1984 | Forsbee et al. |
| 4,539,074 | 9/1985 | Stenberg ............... 162/347 |
| 4,552,619 | 11/1985 | Laitinen et al. ............... 162/336 |
| 4,627,287 | 12/1986 | Suga ............... 73/159 |
| 4,678,075 | 7/1987 | Bowman, Jr. |
| 4,692,213 | 9/1987 | Dove ............... 162/347 |
| 4,735,087 | 4/1988 | Hourani et al. ............... 73/159 |
| 4,832,794 | 5/1989 | Lyytinen ............... 162/336 |
| 4,864,851 | 9/1989 | Haughton ............... 73/159 |
| 4,951,399 | 8/1990 | Ernst ............... 33/706 |

Primary Examiner—William A. Cuchlinski, Jr.
Assistant Examiner—Diego F. F. Gutierrez
Attorney, Agent, or Firm—Spensley Horn Jubas & Lubitz

[57] ABSTRACT

A sheet-gauging apparatus for determining properties of a moving sheet of material includes a frame having parallel upper and lower horizontal supports extending above and below the sheet in a direction transverse to the direction of travel of the sheet. Upper and lower tracks are carried by the upper and lower supports, respectively, each of the tracks including a flat upper surface and a lower surface having tapered end portions. Upper and lower carriages are mounted on the upper and lower tracks, respectively, for bidirectional travel along the tracks, each of the carriages including upper wheels in rolling contact with the upper surface of the track and lower wheels in rolling contact with the tapered end portions of the lower surface of the track. Displacement of the carriages in the directions orthogonal to the direction of carriage travel is thereby minimized. Upper and lower gauging head assemblies disposed on opposite sides of the sheet and coupled respectively to the upper and lower carriages are adapted to measure characteristics of the sheet. The upper wheels have hard, smooth peripheries while the lower wheels have elastomeric tires. Brushes mounted on each carriage outboard of the upper wheels clear debris from the upper surface of the track.

6 Claims, 8 Drawing Sheets

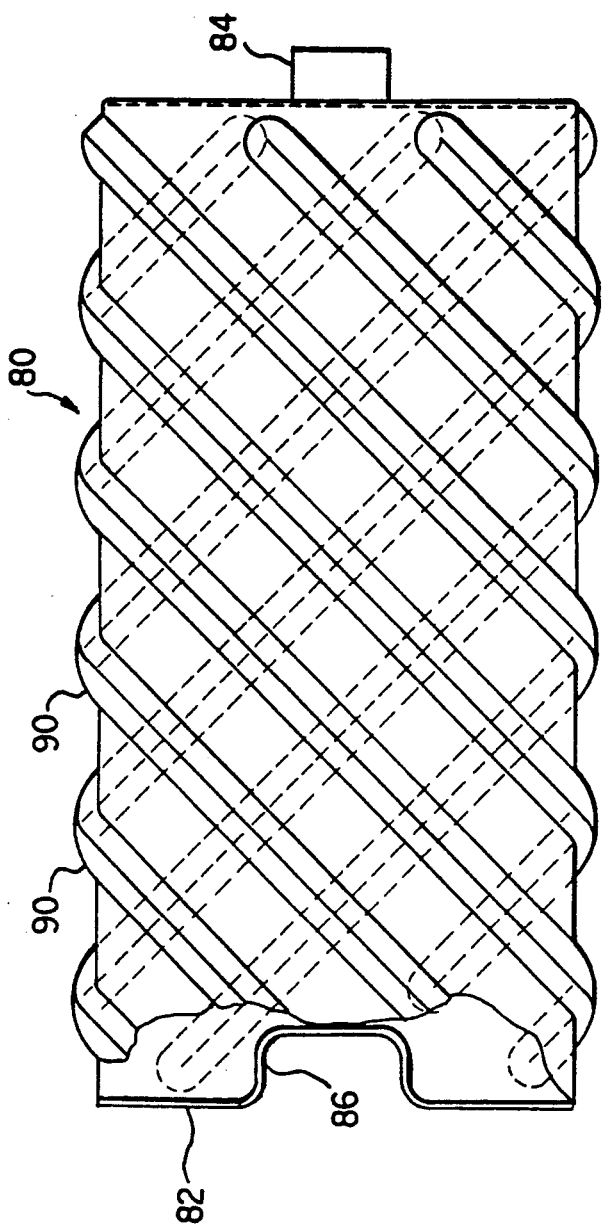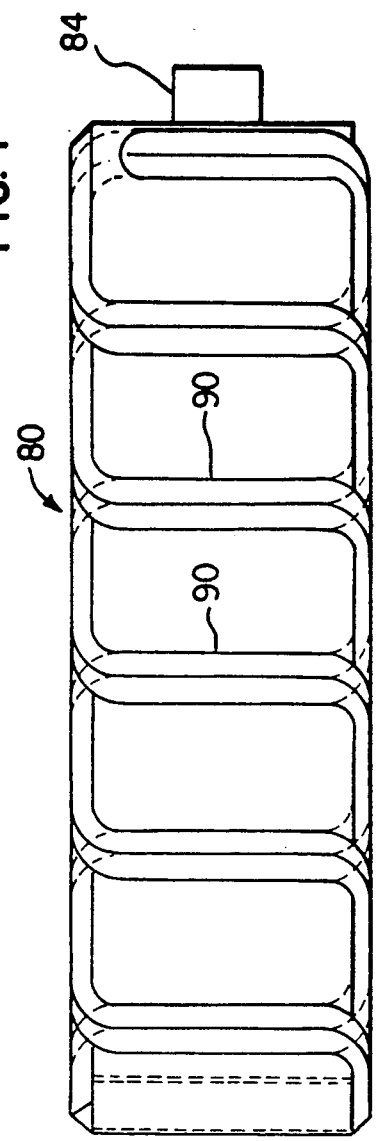
FIG.4
FIG.5

SYSTEM AND PROCESS FOR DETERMINING PROPERTIES OF A MOVING SHEET OF MATERIAL

CROSS REFERENCE TO RELATED

This application is a continuation-in-part of copending application Ser. No. 07/645,949 filed Jan. 25, 1991, for "System and Process for Measuring Properties of a Moving Sheet of Material" which in turn is a continuation-in-part of application Ser. No. 07/575,101 filed Aug. 29, 1990, for "System and Process for Measuring Properties of a Moving Sheet of Material", now abandoned.

BACKGROUND OF THE INVENTION

A common industrial process is the manufacturing of continuous sheets of material, such as paper and plastic, and in order to control the production process sheet-gauging apparatus are used. For example, U.S. Pat. No. 3,621,259 owned by Measurex Corporation teaches a sheet gauging apparatus which includes two beams, one located above the sheet and one located below the sheet. Gauging head assemblies are mounted on the beams and the assemblies include sources and detectors. The sheet gauging apparatus also includes means to reciprocate the gauging head assemblies along tracks carried by the beams to allow measurement of various properties of the sheet at different positions on the sheet. For example, in a paper manufacturing process the moisture content, thickness, basis weight and many other properties of the paper sheet can be measured. It is common in practice for the sheet materials which are being measured by the gauging apparatus to sometimes be quite hot. Radiant heat from the sheet and steam rising from the sheet can cause temperature gradients in the beams which can result in deflection or deformation of the beams and tracks. The deflection or deformation results in variability of the separation of the gauging head assemblies as they travel along the tracks across the sheet which can cause measurement errors.

To reduce deflection and deformation of the beams and tracks, the system taught in U.S. Pat. No. 3,621,259 includes two fans to draw cool air from outside the device and to cause the air to flow longitudinally along the tracks and beams to stabilize the temperature thereof along their entire lengths. However, in some cases this system does not sufficiently reduce deflection of the beams.

Certain techniques are also known to compensate for the variability of the space between the gauging heads. For example, U.S. Pat. No. 4,678,915 owned by Measurex Corporation teaches a device for providing such compensation by determining the separation of the head assemblies and correcting the measured values of the parameter of interest (for example, basis weight, moisture content, and the like) according to the separation of the head assemblies. However, for certain measurements it is desirable to minimize the compensation which is required.

Accordingly, it is an overall object of the present invention to provide an improved system for reducing the thermal deflection and deformation of the beam and tracks in a sheet gauging apparatus.

SUMMARY OF THE INVENTION

In accordance with the broad aspects of the present invention, a sheet-gauging apparatus is provided for determining properties of a travelling sheet such as a paper web. The apparatus comprises a gauging head assembly adapted to scan the sheet and measure certain characteristics thereof. The properties to be determined are related to the measured characteristics. The gauging head assembly is carried by a support which defines a fluid-conducting channel. Means, such as a motor driven pump, causes fluid to flow in the channel, the flowing fluid reducing temperature gradients between different parts of the support to reduce deflection or deformation thereof.

In accordance with another aspect of the invention, inserts may be disposed within the support channel for defining a fluid conduction passage having a flow cross section substantially smaller than that of the channel. The inserts, which are disposed end-to-end within the channel, preferably include outer, spiral ridges projecting into the fluid conduction passage for inducing turbulence in the flowing fluid.

Pursuant to yet another aspect of the invention, the support carrying each gauging head assembly includes a beam and a track supported by the beam. The track, seen end-on, has a uniform cross-section including a flat upper surface and a lower surface having tapered end portions. The head assembly is mounted on a carriage including on each side thereof a pair of upper wheels riding in rolling contact on the upper surface of the track and a pair of lower wheels, set at an angle, riding in rolling contract on the surfaces of the corresponding tapered end portions. The wheels are precision components mounted so as to be in close tolerance engagement with the surfaces of the track on which they ride. Motion or "play" in the directions orthogonal to the direction of travel is thereby minimized. The smooth, linear surfaces of the track assure precise and accurate linear motion of the gauging head assembly. Further in this connection, the track is secured to the support beam in such fashion that relative thermal expansions and contractions of the track and beam do not cause deformation or distortion of the track.

Because debris such as dust, lint or other particles tends to settle on the flat upper surface of the track and impede the rolling of the upper wheels, in accordance with yet another feature of the invention the lower wheels are preferably provided with rubber tires furnishing a small amount of "give" or resilience to allow the smooth, hard, upper wheels to roll over any debris. Moreover, to minimize the collection of such debris, a brush is mounted at each end of the head assembly carriage ahead of each upper wheel to continuously wipe clean the upper surface of the track as the carriage moves back and forth therealong.

BRIEF DESCRIPTION OF THE DRAWINGS

Further objects, features and advantages of the invention will become apparent from the detailed description which follows when taken in conjunction with the accompanying drawings in which:

FIG. 4 is a side elevation view of an insert which may be placed within a flow channel formed in the support structure of the apparatus of the invention;

FIG. 5 is a plan view of the component shown in FIG. 4;

DESCRIPTION OF THE PREFERRED EMBODIMENTS

Figure 1:
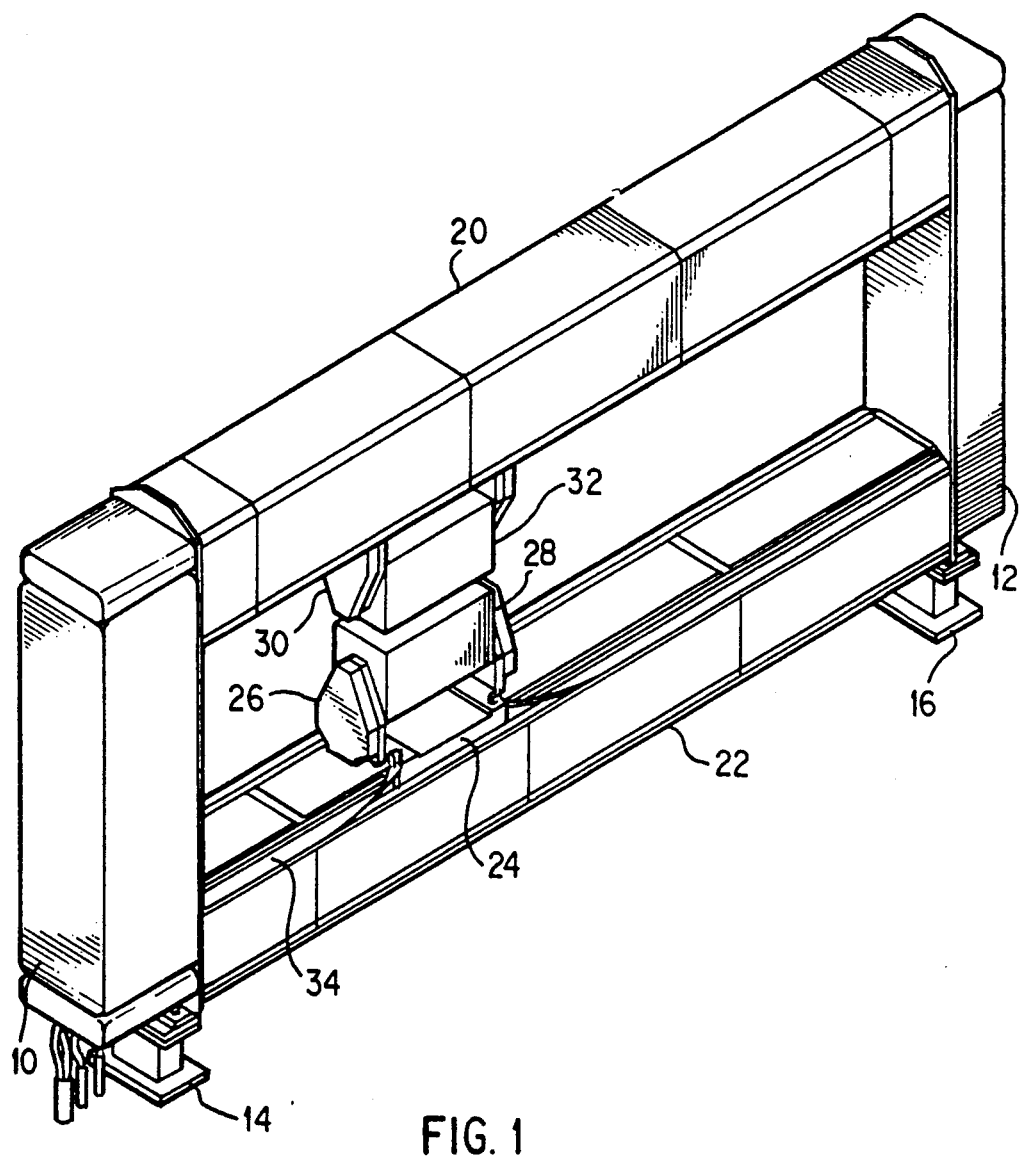
FIG. 1 is an isometric view of a sheet-gauging apparatus incorporating the present invention.

A preferred embodiment of the sheet-gauging apparatus is shown in FIG. 1. The embodiment shown in FIG. 1 includes a left housing 10 and a right housing 12 which are vertically mounted on left base 14 and right base 16, respectively. In practice the bases 14 and 16 are secured to a solid surface such as the floor of a paper-making facility.

An upper, horizontal housing 20 is disposed between the left housing 10 and the right housing 12 and a lower, horizonal housing 22 is located between the housings 10 and 12. The lower housing 22 is parallel to the upper housing 20 and vertically spaced apart therefrom. A lower carriage 24 is mounted on the lower housing 22, and similarly, an upper carriage, not shown, is connected to the bottom of the upper housing 20. Two lower head supports 26 are coupled one to either end of the lower carriage 24, and a lower head assembly 28 is mounted between the lower head supports 26. Similarly, there are two upper head supports 30 coupled to the upper carriage assembly, not shown, and an upper head assembly 32 is connected between the upper head supports 30. Seals 34 are connected to the lower housing 22 and the upper housing 20. The seals 34 are flexible and help to prevent material from entering the interior of the housings 20 and 22.

Figure 2:
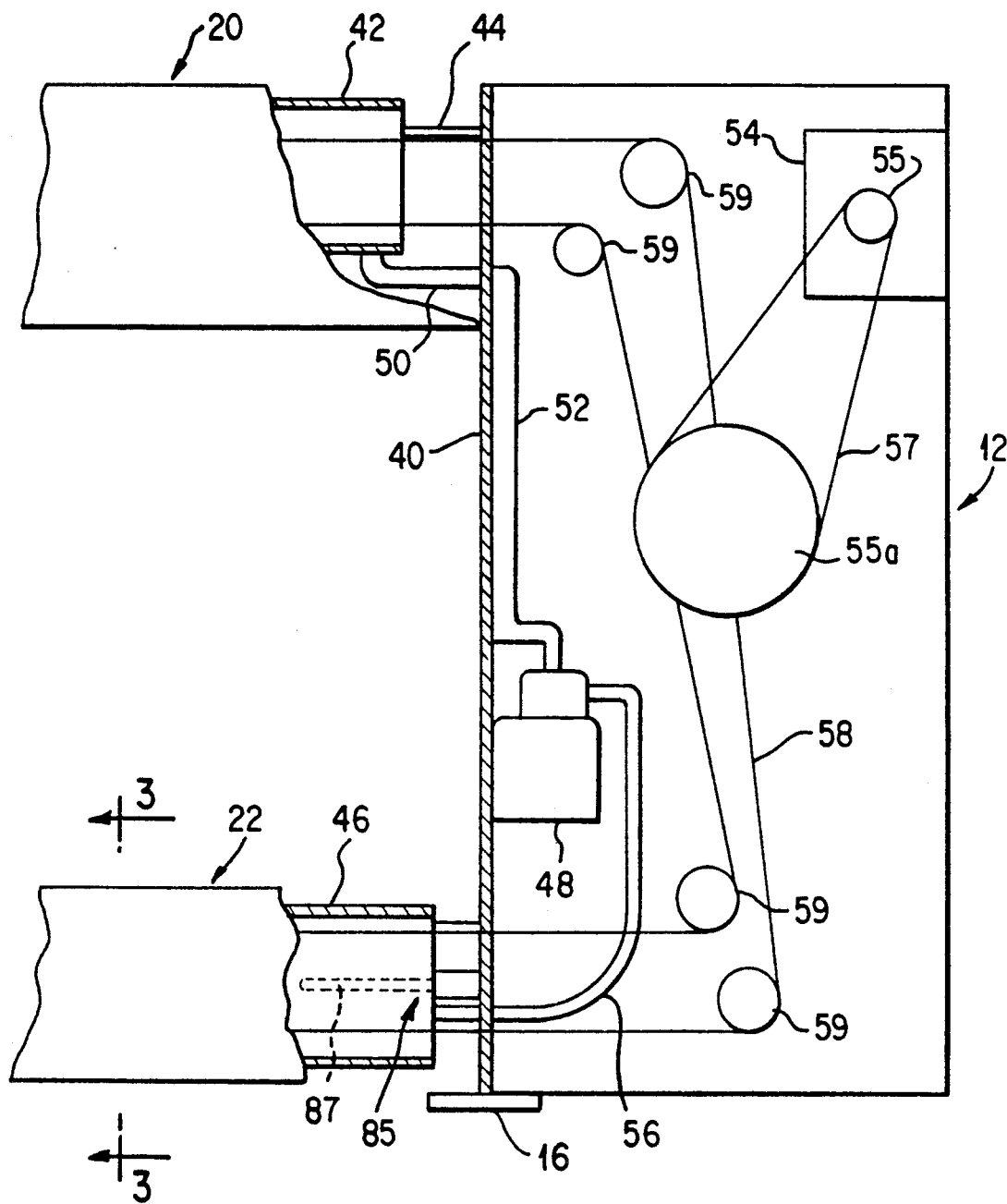
FIG. 2 is a front elevation view of one portion of the system shown in FIG. 1, with part of the housing broken away and portions thereof shown in cross section.

FIG. 2 shows the right hand ends of the upper and lower housings 20 and 22 and components of the device located within the interior of the right housing 12. Part of the housing 12 has been cut away to show interior components, and similarly the right ends of housings 20 and 22 have been broken away to show components located inside. A vertical support 40 is located within the right housing 12, and the vertical support 40 is a rectangular plate mounted on the right base 16. An upper, horizontal support 42 is coupled to the top end of the vertical support 40 by connecting bracket 44, and similarly a lower, horizontal support 46 is coupled by a connecting bracket to the lower end of the vertical support 40. The upper support 42 and lower support 46 extend substantially horizontally between the vertical support 40 at the right end of the device and another vertical support, not shown, which is located in the left housing 10. The horizontal supports 42 and 46 and vertical support 40 and the vertical support located inside housing 10 together form a frame.

A pump and motor assembly 48 is connected to the vertical support 40, and a conduit 50 is connected to lower side of the upper support 42 to provide fluid communication between the interior of the upper support 42 and a pipe 52 which is mounted on the vertical support 40. The pipe 52 is mounted in contact with the vertical support 40 to provide thermal, heat transfer communication between fluid within the pipe 52 and the vertical support 40. The lower end of pipe 52 is connected to the pump and motor assembly 48. Pipe 56 is connected to the pump and motor assembly 48 to carry fluid therefrom into the interior of the lower support 46.

Enclosed in the housing 12 is a drive means to cause the carriages, not shown, to travel back and forth along tracks 66 (seen in FIG. 3) mounted on the supports 42 and 46. The drive means includes a motor 54 mounted on to the inside of housing 12, and a drive sprocket 55 on the motor 54. A belt 57 travels around the sprocket 55 and around driven sprocket 55a which drives another belt 58. The belt 58 travels around idle rollers 59, and the lower part of belt 58 travels through the lower housing 22 and is connected to the lower carriage 24. The belt 59 travels around a similar set of rollers located in the left housing 10. Accordingly, the motor is operable to drive the lower carriage 24 in a reciprocating fashion along the lower support 46. Similarly, the motor simultaneously drives the upper carriage along the upper support 42 in unison with the lower carriage 24.

Figure 3:
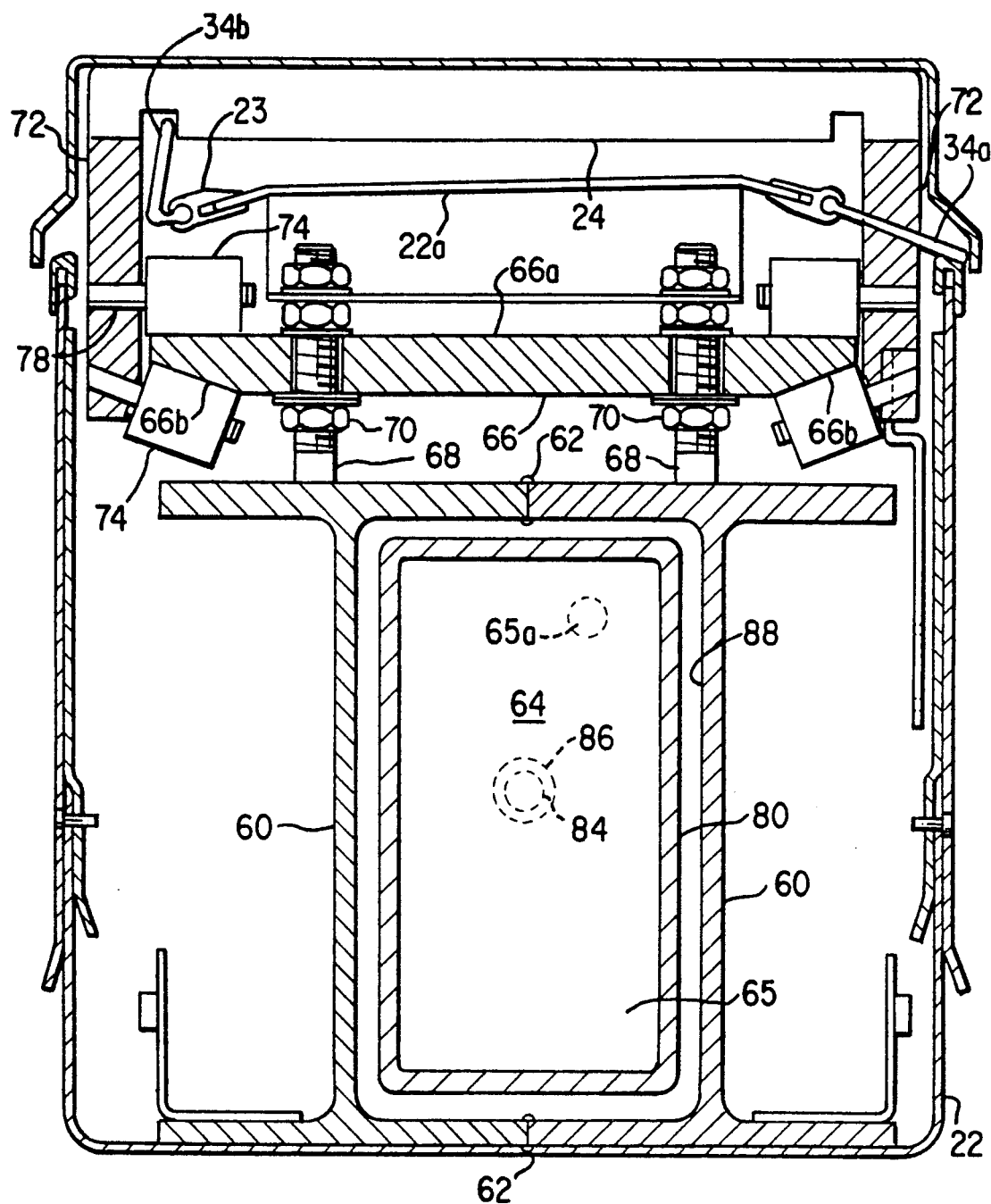
FIG. 3 is a cross section view taken along line 3—3 of FIG. 2.

Turning now to FIG. 3, there is shown a section of the lower housing 22 and lower support 46 taken along line 3—3 in FIG. 2. As shown in FIG. 3, the lower support 46 includes two I beams 60 which are welded together at seams 62. The seams 62 are continuous along the length of the I beams so that a water tight channel 64 is formed between the two I beams 60. A horizontal track 66, parallel with and spaced apart from the I beams 60, is secured to the beams 60 by studs 68 and nuts 70.

The track 66 has a flat upper surface 66a while the lower surface thereof has tapered end portions 66b. The track 66 has a uniform cross section along its entire length. The lower part of the lower carriage 24 is shown in FIG. 3, but for clarity the upper portions of the lower carriage 24 are not shown. The lower carriage 24 has two arms 72 which depend from either side thereof and extend adjacent the outer edges of the track 66. Two wheels 74 are mounted on the lower part of each arm 72 by axles 78. The wheels 74 are located and oriented so that they snugly engage the outer end portions of the upper surface 66a and the tapered end portions 66b of the lower surface of the track 66. It will be appreciated that the combination of the upper wheels 74 riding along the flat upper surface 66a of the track 66 and the lower wheels 74 set at an angle and riding along the tapered end portions 66b of the lower surface of the track, prevent lateral and vertical displacements (as viewed in FIG. 3) of the carriage relative to the track. Accordingly, the lower carriage 24 can travel smoothly and linearly along track 66 in precise alignment therewith. As the lower carriage 24 travels, the seals 34 are forced upward to accommodate the arms 72, and after the carriage 24 passes, the seals 34 resume the position shown in FIG. 3. The interior edges of seals 34 are coupled to the upper members 22a of the housing 22 by connectors 23, throughout the length of the housing 22.

The exterior edges of seals 34 are free to move up and down so that normally the seals 34 are in the position indicated as 34a to prevent dirt from entering the housing 22, and when the carriage 24 is adjacent a particular portion of the seals, that portion is deformed into the position indicated as 34b. Rollers, seals into positions 34a and 34b.

The ends of channel 64 are sealed by plates, such as the plate 65. A port 65a is formed in the plate 65 at the end of the lower support 46 located adjacent the left housing 10 to permit fluid to exit from the channel 64 and flow through a pipe, not shown, which is connected to a similar port in the upper support 42.

It should be understood that upper support 42 is substantially identical to the lower support 46, except that the upper support 42 is inverted relative to the orientation of support 46.

Turning to FIGS. 4 and 5 there is shown fluid displacement and turbulence means. The fluid displacement and turbulence means includes an insert or hollow member 80 which has thin walls 82. A screw-on cap 84 is connected to one end of the hollow member 80 by means of threaded connection, not shown. A corresponding indentation 86 is formed in the end of the hollow member 80 opposite the cap 84, and the indentation 86 is sized slightly larger than the cap 84. A plurality of ridges 90 are formed on the outer surface of the hollow member 80, and the ridges form a generally spiral pattern along the length of the exterior of the hollow member 80.

With reference to FIG. 3, a plurality of inserts or hollow members 80 are inserted end to end in the channel 64. The cap 84 of each hollow member 80 fits within the corresponding indentation 86 of the adjacent hollow member 80. The hollow members 80 and their ridges 90 are so dimensioned and located that when the members 80 are within the channel 64 the outer edges of the ridges 90 contact the internal surfaces of the I beams 60. The internal surfaces of the beams 60, the inserts 80 and the ridges 90 thereby define a spiral fluid conduction passage 88, substantially smaller in cross section than the channel 64, throughout the length of the support 46. Likewise, a series of inserts 80 are inserted in the corresponding channel in the upper support 42 to form a spiral passage similar to the passage 88 in the channel 64 of the lower support 46.

The liquid conduction system including passage 88, the corresponding passage in the upper support 42, and the pump and piping, is filled, in accordance with one form of the invention, with a mixture of water and automobile-type antifreeze. The pump and motor assembly 48 continuously circulates the mixture through the supports 42 and 46.

It is common in practice that sheet materials being measured by the gauging apparatus can be quite hot. Hot vapor such as steam sometimes rises from the sheet and radiant heat from the sheet can also affect the supports. Moreover, interruptions in the production of the sheet can result in temporary cooling of the supports. Hot vapor and radiant energy from the sheet tends to heat the lower portions of the upper support 42 substantially more than the upper portions thereof. Similarly, those portions of the lower support 46 which are nearest the sheet are more affected than portions which are further away. Temperature gradients in the supports can result in significant deflection and/or deformation of the supports. However, we have found that in the present embodiment the temperature gradients in the supports are substantially reduced since heat is transferred from the relatively hotter portions of the supports to the flowing fluid and thereafter to cooler portions of the supports. Accordingly, deflection and deformation of the supports is reduced. Without the present invention, thermal gradients can also occur in the vertical supports 40 and cause deflection and deformation of the gauging apparatus, and such gradients are reduced by the present invention.

We have found that the ridges 90 on the hollow members 80 create sufficient turbulence in the fluid to enhance the heat transfer capability of the system and thereby reduce thermal gradients between portions of the supports 42 and 46. We have also found that the hollow members 80 provide added advantages. In practice, we have found it desirable to seal the fluid contained in the system consisting of the supports 42 and 46 and the pump and piping 40, 50 and 52. When the system is sealed air cannot mix with the fluid and corrosion of the I beams is thereby reduced. However, if the hollow members 80 were not used, sealing the system would not be practical because of thermal expansion and contraction of the fluid due to the wide temperature variations experienced by the system. But since the hollow interiors of members 80 are filled with air, they expand and contract as necessary to accommodate thermal expansion and contraction of the fluid. Another advantage of the hollow members 80 is that their use results in a significant reduction in the amount of fluid which is necessary since only the spiral passage 88 contains fluid. The amount of fluid is, of course, substantially less than what would be required if the channels 64 were completely filled.

Optionally, the system can include means to heat the liquid inside the channel 64. With reference to FIG. 2, the heating means includes an electrically powered heater 85 which is mounted on the vertical support 40 and has a resistive heating element 87 which extends a short distance into the channel 64. In certain cases the heater 85 may be used to keep the upper and lower supports 42 and 46 above ambient temperature. For example, when the sheet-making process is temporarily suspended, it may be useful to operate the heater 85 and the pump 48 to keep the supports 42 and 46 at about the temperature they would be when the sheet making process is operating. Thus, when production is resumed the supports will not be heated and undergo deformation. Also, the heater 85 may be used to keep the supports above the dew point temperature thereby preventing condensation of water on the supports, which could result in water droplets falling on the sheet.

Although in the system shown in FIG. 1 the upper housing 20 and the lower housing 22 are substantially horizontal, it should be understood that the present invention is also applicable to sheet-making processes wherein the sheet and/or housings 20 and 22 are disposed vertically or at some other angle.

It should also be understood that although the preferred embodiment is described herein as applied to a device which is sometimes called an "O-frame" scanner due to the shape defined by the housings, other types of scanners are also sometimes used, and the present invention is equally applicable to those other types as well. For example, in addition to the conventional "O-frame" scanner there is also a design called a "C-frame" scanner which is similar to the "O-frame" scanner except that it has only one end housing. The carriages and head assemblies in a "C-frame" scanner do not move relative to the upper and lower supports 40 and 42. Rather, in a "C-frame" scanner the head assemblies are fixed relative to the support members, and the support members along with the head assemblies are driven to reciprocate back and forth across the sheet. A C-frame scanner is taught, for example, in U.S. Pat. No. 3,840,302.

Figure 6:
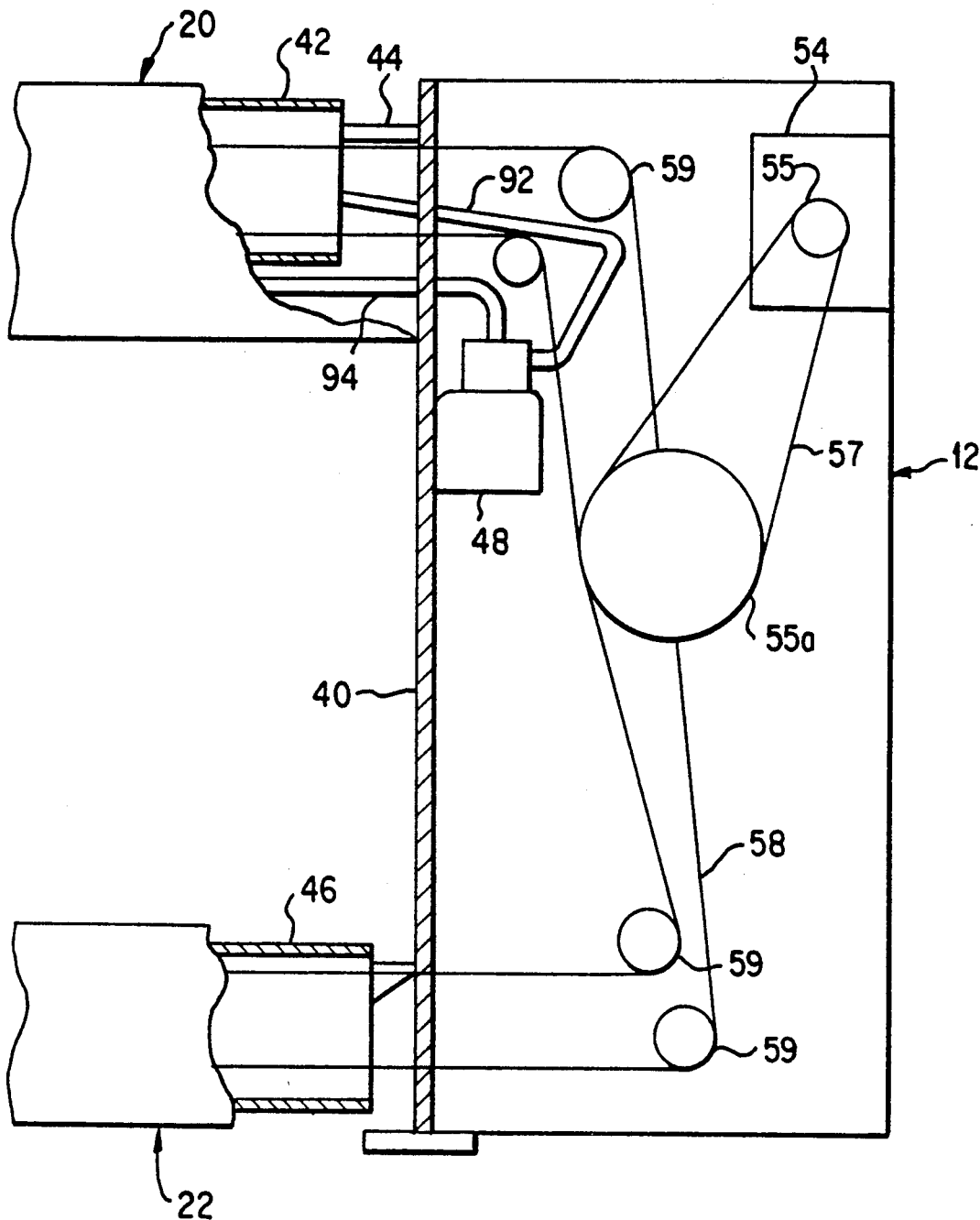
FIG. 6 is a front elevation view, like that of FIG. 2, showing an alternative embodiment of the present invention.

In some circumstances it may be necessary to circulate liquid only in one of the supports 42 or 46. FIG. 6 illustrates such an alternative embodiment, in which the pump and motor assembly 48 is connected by a pipe 92 to receive fluid from the right end of support 42. Liquid from the pump 48 flows through a pipe 94 located inside the housing 20 to the left end of the support 42 where it enters the support 42 to flow through the channel inside support 42.

It should be noted that the track 66 is normally made of fiberglass and that liquid is not circulated through the track. This can result in differences in thermal expansion and contraction between track 66 and the support 42 or 46 to which it is attached.

In some scanner systems, particularly longer ones, we have found that this can cause undesirable deformation of the track 66 since the tracks are bolted to the supports. However, any such problems can be overcome by the system shown in FIGS. 7-10.

Figure 7:
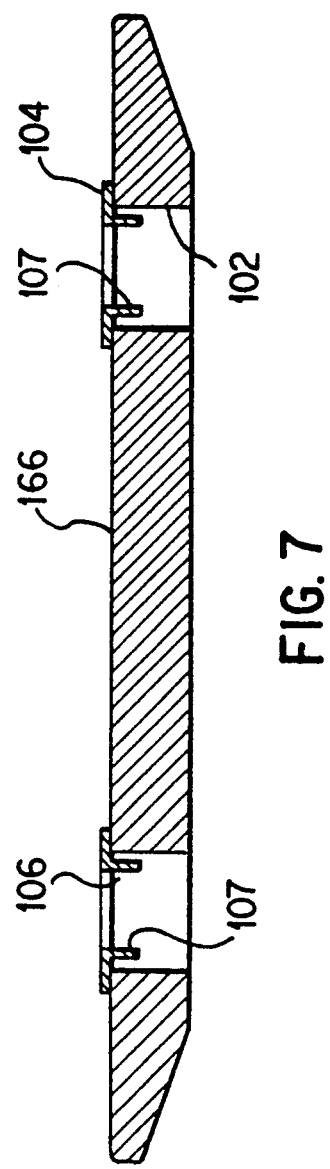
FIG. 7 is a side elevation view, in cross section, of an alternative embodiment of a track which may be used in the system of the present invention.
Figure 9:
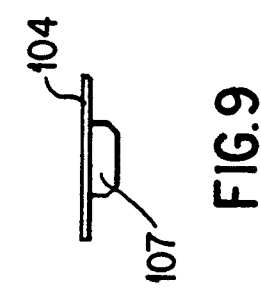
FIGS. 8 and 9 are details of a mounting bracket used in connection with the track of FIG. 7.

FIG. 7 shows a cross section of an alternative track 166 having a plurality of holes 102 for attachment to the studs 68. The holes 102 are somewhat larger than the studs 68, and metal brackets 104 are fitted into the holes 102. Each metal bracket 104, one of which is shown in detail in FIGS. 8 and 9, has a hole 106 which is generally rectangular. The long sides of the hole 106 have depending tabs 107. The brackets 104 are pressed into the fiberglass track 166 so that they are permanently attached to the track 166 with the long dimension of the hole 102, and the tabs 107, oriented along the length of the track 166.

Figure 8:
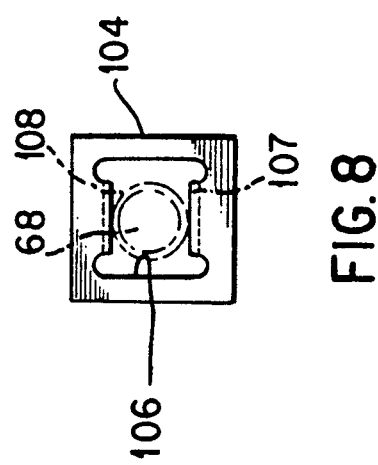
Figure 10:
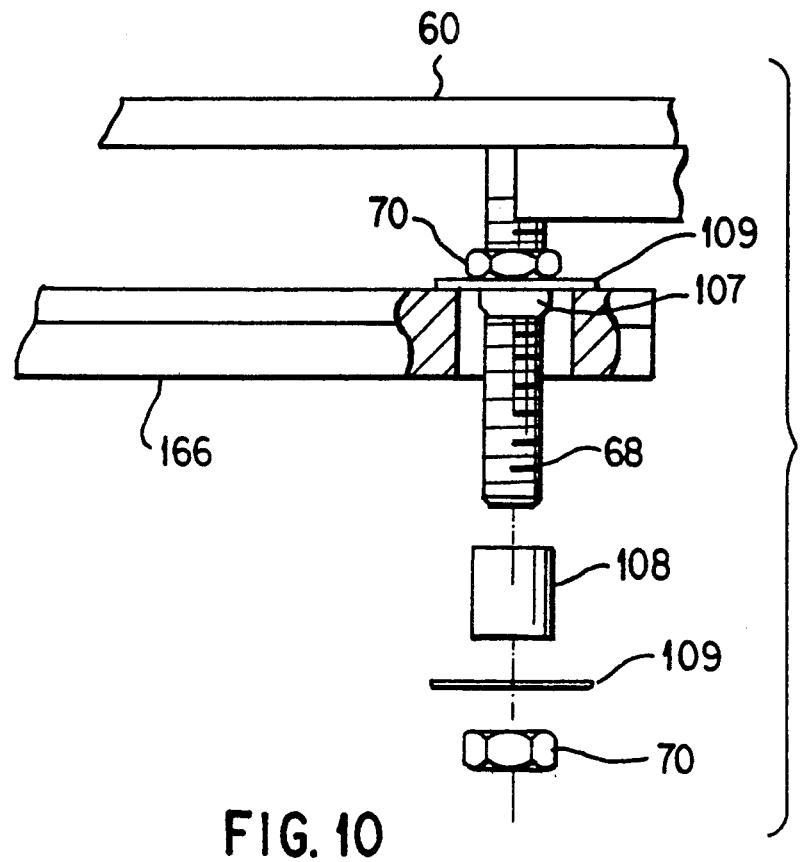
FIGS. 10 and 11 are front and side elevation views, respectively, partly in cross section, of the alternative embodiment of FIGS. 7-9 showing details of the mounting arrangement.
Figure 11:
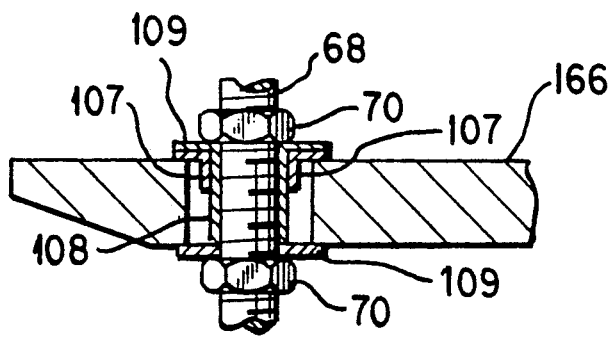

When the track 166 is assembled to the studs 68, a bushing 108 is located around each stud as shown in FIGS. 10 and 11. (FIG. 10 shows the track 166 in the upper housing 20.) The outside diameter of the bushing is the same as the short dimension of the hole 106, while the long dimension of the hole 106 is, of course, longer than the diameter of the bushing. (FIG. 8.) The length of the bushing is slightly greater than the thickness of the track 166. Accordingly, when the nuts 70 are tightened against the bushings 108 and washers 109 the track 166 can move relative to the studs and the I beams 60 in the dimension parallel to the length of the track 166, but the track 166 cannot move relative to the beams 60 in the other two dimensions. Accordingly, when the beams 60 and the track 166 expand or contract relative to one another, they move relative to one another only in the dimension along the track so that the track 166 is not deformed.

Figure 12:
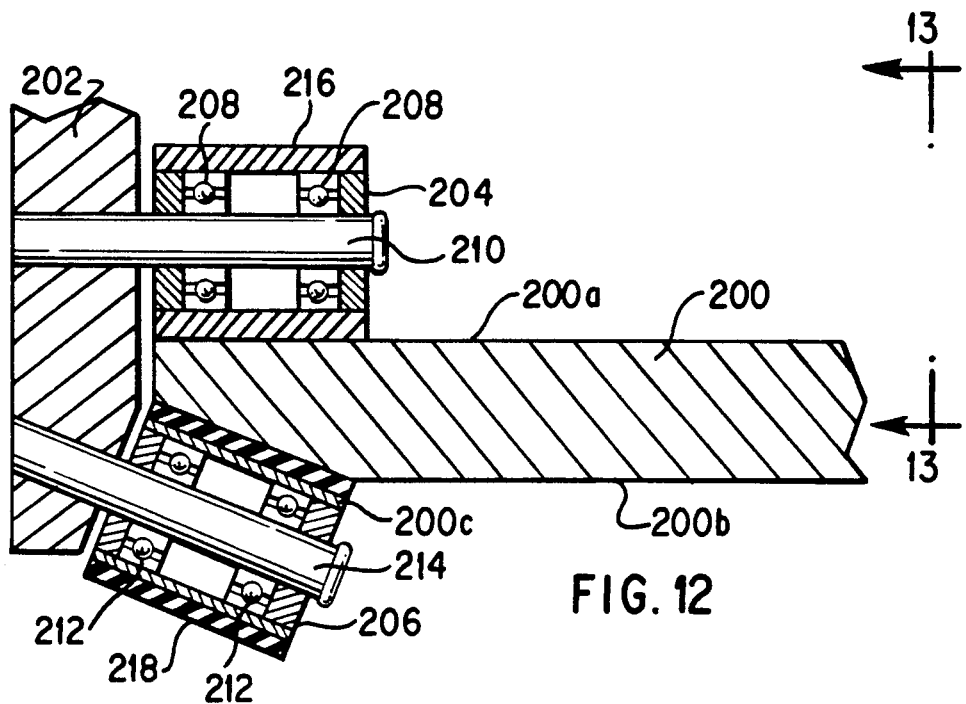
FIG. 12 is a cross section view, similar to FIG. 4, showing details of a carriage support wheel assembly in accordance with another embodiment of the invention.
Figure 13:
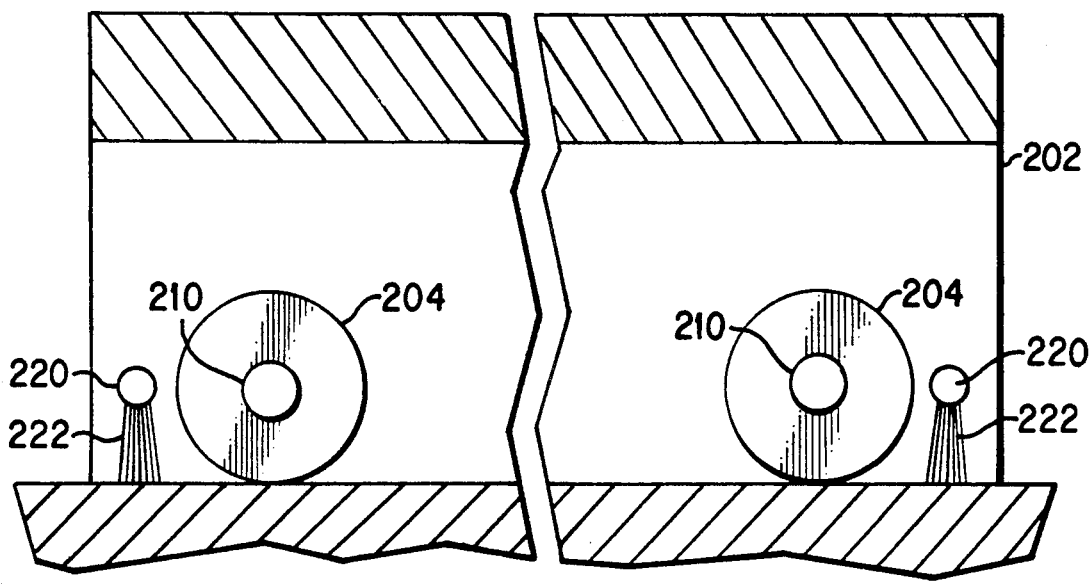
FIG. 13 is a front elevation view, partly in cross section, as seen along line 13—13 in FIG. 12.

FIGS. 12 and 13 show another embodiment of the invention assuring accurate linear motion of the upper and lower carriages and hence the sheet-gauging head assemblies mounted thereon. In FIGS. 12 and 13 there is shown a horizontal track 200 of uniform cross section along its entire length including a flat upper surface 200a and a lower surface 200b having tapered end portions 200c only one of which is shown in FIG. 12. By way of example, the end portions 200c may each be inclined at an angle of about 20 degrees from the horizontal.

A sheet-gauging head assembly carriage having side arms 202 (only one of which is shown in FIGS. 12 and 13) is adapted to move along the track in a precise linear path as already explained. In this connection, mounted on each side arm 202 is a pair of longitudinally spaced upper wheels 204 riding in rolling contact with the upper surface 200a of the track 200 and a corresponding pair of longitudinally spaced lower wheels 206, set at an angle corresponding to that of the tapered surfaces 200c, riding in rolling contact with said tapered surfaces.

Each upper wheel 204 is rotatably mounted on a pair of ball bearings 208 received by a shaft 210 pressed in place in the side arm 202. Likewise, each lower wheel 206 is rotatably mounted on ball bearings 212 received by a shaft 214 oriented at an angle corresponding to that of the tapered surface 200c and pressed in place in the side arm 202. Each of the upper wheels 204 has an outer ring 216 of Delrin or the like having a smooth, relatively hard outer surface in rolling contact with the upper surface of the track. In contrast, each of the lower wheels is provided with an outer elastomeric tire 218 in rolling contact with the corresponding tapered surface 200c. The tires, which may be rubber, provide a limited amount of "give" or resilience thereby enabling the upper wheels to ride over debris, such as lint, dust or other particles, that tends to accumulate on the upper surface of the track as a result of the processing of the sheet material.

The accumulation of debris on the upper track surface 200a that might interfere with the unimpeded rolling of the upper wheels is minimized in accordance with another aspect of the invention shown in FIG. 13. Projecting inwardly from each end of the side arm 202 adjacent to and outboard of each upper wheel 204, is a bar 220 carrying a brush 222 in wiping contact with the upper track surface. The length of the brush is approximately equal to that of the wheel 204 s that the entire portions of the track traversed by the upper wheels is wiped clean by the brushes as the carriage moves back and forth along the length of the track.

What is claimed is:

1. A sheet-gauging apparatus for determining properties of a moving sheet of material, the sheet having a direction of travel, the apparatus comprising:
  a) a frame having parallel upper and lower horizontal supports extending above and below the sheet in a direction transverse to the direction of travel of the sheet;
  b) upper and lower tracks carried respectively by the upper and lower supports, each of the tracks having a flat upper surface and a lower surface having tapered end portions;
  c) upper and lower carriages mounted respectively on the upper and lower tracks for bidirectional travel along said tracks, each of the carriages including upper wheels in rolling contact with the upper surface of the track and lower wheels in rolling contact with the tapered end portions of the lower surface of the track, motion of the carriages in the directions orthogonal to the direction of carriage travel being thereby minimized;
  d) upper and lower gauging head assemblies disposed on opposite sides of the sheet and coupled respectively to the upper and lower carriages for measuring characteristics of the sheet; and
  e) drive means connected to the carriages for reciprocating the gauging head assemblies along the tracks and laterally of the sheet.

2. Apparatus according to claim 1, wherein:

a) the upper wheels have smooth, hard outer surfaces in contact with the upper surface of the track; and
b) the lower wheels have elastomeric tires, whereby the resilience of the tires allows the upper wheels to roll over any debris accumulated on the portions of the upper surface of the track traversed by the upper wheels.

3. Apparatus according to claim 1, wherein:
a brush is mounted on the carriage outboard of each of the upper wheels, the brushes being in wiping contact with the portions of the upper track traversed by the upper levels so as to clear debris from the upper surface of the track in both directions of travel of the carriage.

4. Apparatus according to claim 1 including:
liquid conduction means coupled to the frame to cause liquid to flow in thermal communication with the frame thereby reducing temperature gradients between different parts of the frame to minimize thermal deflection and deformation thereof.

5. Apparatus according to claim 4 in which:
each of the tracks is attached to a corresponding support by fastener means passing through holes in said track, said holes being larger than said fastener means, said track and support being thereby adapted to thermally expand and contract relative to each other preventing deformation of said track.

6. Apparatus according to claim 5 including:
means received by each hole for limiting relative movement of said track and support to a direction along the length of said track as a result of said expansion or contraction.

* * * * *